United States Patent [19]

Storz

[11] Patent Number: 4,607,620
[45] Date of Patent: Aug. 26, 1986

[54] MEDICAL GRIPPING INSTRUMENT

[76] Inventor: Karl Storz, Auf Den Schildrain 39, Tuttlingen, Fed. Rep. of Germany

[21] Appl. No.: 555,372

[22] Filed: Nov. 28, 1983

[30] Foreign Application Priority Data

Feb. 8, 1983 [DE] Fed. Rep. of Germany ... 6803342[U]

[51] Int. Cl.⁴ ............................................. A61B 17/28
[52] U.S. Cl. ......................................... 128/4; 128/321
[58] Field of Search .................... 128/321, 303.15, 3–8

[56] References Cited

U.S. PATENT DOCUMENTS

| 2,002,594 | 5/1935 | Wappler | 128/321 |
| 2,034,785 | 3/1936 | Wappler | 128/4 |
| 4,027,510 | 6/1977 | Hiltebrandt | 128/6 |
| 4,386,602 | 6/1983 | Sheldon et al. | 128/4 |
| 4,471,766 | 9/1984 | Terayama | 128/6 |

Primary Examiner—William R. Dixon, Jr.
Assistant Examiner—Steven Capella
Attorney, Agent, or Firm—Donald D. Mon

[57] ABSTRACT

A medical gripping instrument for endoscopy. A sleeve has a passage with a distal opening. A periscope extends axially in this passage, along with at least three springy gripping arms, which also are axially movable. They leave a clear path between them so the periscope can see what they grasp. The arms and periscope are linked so that both move axially simultaneously so the region in the arms remains in the view of the periscope, and an object brought into the shaft by the arms will not harm the periscope.

2 Claims, 6 Drawing Figures

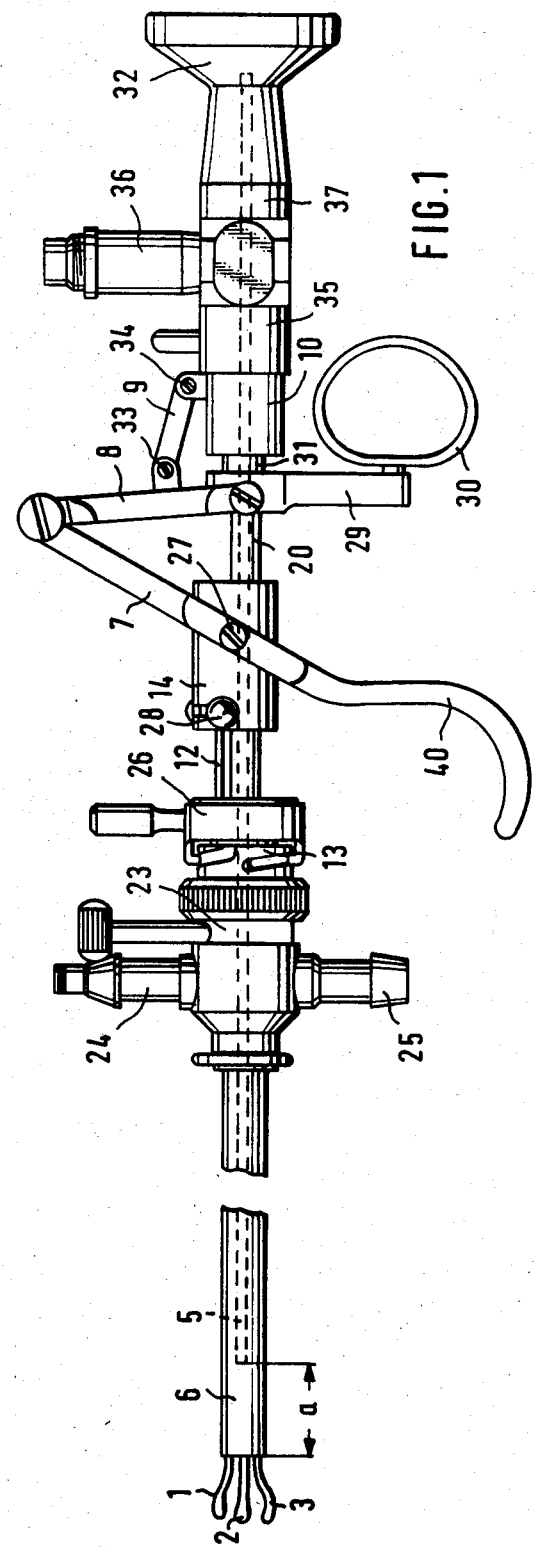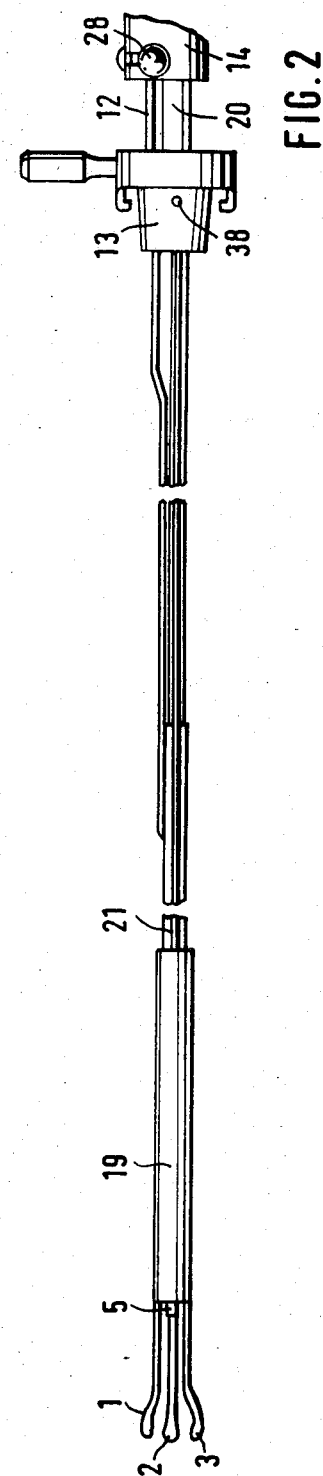

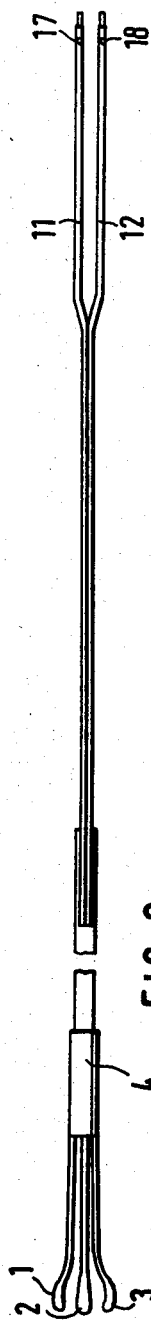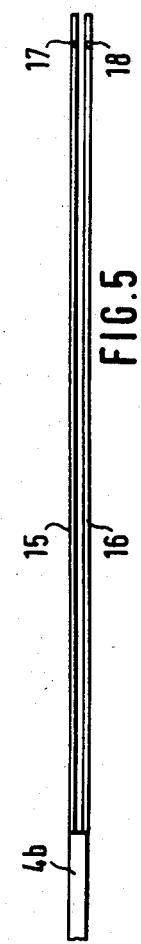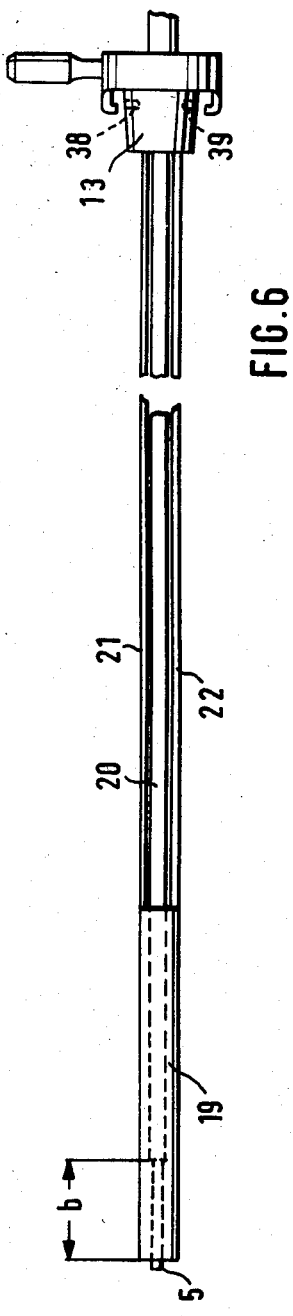

MEDICAL GRIPPING INSTRUMENT

BACKGROUND OF THE INVENTION

The invention relates to a medical gripping instrument for use with endoscopes.

Known instruments of this type generally have at least two parallel ducts or channels in a common endoscope shaft which envelopes the same. One of the two ducts contains the periscope or viewing tube, whilst the other duct arranged eccentrically to the complete endoscope shaft contains a sleeve containing the resilient gripping arms. By means of the rods at the proximal end of the endoscope, said arms can be displaced with respect to the sleeve, so that they are moved out of the latter to the front and extend laterally with respect to the said sleeve. Generally, there are three such gripping arms, which are drawn back into the sleeve by a spring at the proximal end and are consequently returned to their closed position. This firstly leads to the disadvantage that the gripping arms are arranged eccentrically to the periscope, so that when operated in the vicinity of the distal end, they cannot be seen or can only be partly seen through the periscope. Another disadvantage results from the fact that the endoscope shaft as a whole must be relatively thick, because it has to receive at least the two parallel ducts.

In addition, an endoscope with a longitudinally displaceable wire loop is known, in which the connection of the telescopic periscope with the loop takes place by means of a gear in such a way that the periscope is displaced less than the wire loop. This permits the use of a telescopic periscope with a wide field of view, substantially without impeding vision through the edge of the endoscope shaft (Germany DOS No. 2,628,555).

SUMMARY OF THE INVENTION

The problem of the invention is to obviate the aforementioned disadvantages and to so improve the endoscope of the initially described type, that the gripping arms are always in the visual range of the periscope.

As a result of the concentric arrangements of the sleeves, not only is the aforementioned problem solved, but also space is saved, so that the endoscope shaft can have a smaller external diameter.

Following of the periscope on the one hand ensures that the periscope objective or lens always remains in the vicinity of the point to be observed in the good visual range of the gripping arms, whilst on the other hand ensuring that there is no risk of the objective being damaged by a stone withdrawn by the gripping arms. Sufficient space is provided at the distal end for receiving such stones or foreign bodies in the endoscope shaft.

This invention provides the advantage that, the doctor consequently has the possibility of easily closing the gripping arms prior to insertion into the endoscope shaft, by operating with the right hand, to the extent that they can easily be introduced into said shaft. It would otherwise be necessary to compress the gripping arms by hand, in order to introduce the instrument into the shaft, for which purpose a second person would be required to hold the shaft.

BRIEF DESCRIPTION OF THE DRAWINGS

The invention is described in greater detail hereinafter relative to non-limitative embodiments and with reference to the attached drawings, wherein show:

FIG. 1 a side view with a greatly shortened endoscope shaft on the complete instrument.

FIG. 2 a side view of part of the instrument with the endoscope shaft dismantled.

FIG. 3 a side view of the first embodiment of the actuating or operating sleeve.

FIG. 4 a view as in FIG. 3 of a further embodiment.

FIG. 5 a partial view of the embodiment of FIG. 4, but rotated by 90°.

FIG. 6 a view as in FIG. 2, but after dismantling the operating sleeve.

DETAILED DESCRIPTION OF THE INVENTION

FIG. 1 shows the instrument in an intermediate position, in which gripping arms 1, 2, 3 are not completely extended. However, they are not completely retracted into endoscope shaft 6 and instead still project by a small amount to the left over the end of shaft 6. As can be seen, they spring outwards and are arranged completely centrally with respect to shaft 6.

Shaft 6 contains a plurality of sleeves, which have been omitted so as not to overburden the drawing. By means of interrupted lines, the very thin or slender periscope of viewing tube 5 is indicated, whose distal end in this position is at a distance a from the distal end of shaft 6. On moving the gripping arms further to the left, the objective or lens of periscope 5 is also moved further to the left, as will be explained hereinafter.

Further to the right, it is possible to see the shaft closure 13 with the conventional bayonet ring 23. It is an advantage of this embodiment that use can be made of a conventional endoscope shaft with rinsing connections 24, 25. As will be explained hereinafter, bayonet lock ring 26 forms part of the shaft closure 13.

Further to the right, it is possible to see wire 12 and below it the fixed sleeve 20 for periscope 5. Further to the right can be seen slide 14, which, can be slidingly moved to the right by spring tension on fixed sleeve 20 through the two levers 7 and 8. Such lever systems are known per se and need not therefore be represented in detail. At the bottom, lever 7 terminates in a handle and is mounted so as to pivot around screw 27. A locking device 28 is provided at the top left of slide 14, so as to permit the detachable fixing of operating wires 11, 12 in said slide. These wires are best shown in FIG. 3. Lever 8 is pivoted at the top on the vertical fixed part 29, to which is fixed at the bottom handle 30 for inserting the thumb.

Sleeve 10, together with the remainder of the endoscope located to the right with eyepiece 32 is movable on the fixed sleeve 31 by lever 9, which is articulated at its ends 33, 34 to sleeve 10 or lever 8. When slide 14 moves to the left, sleeve 10 follows this movement to a reduced extent. Such gears are known per se and need not therefore be described in detail.

By means of bayonet ring 35, eyepiece 32 is connected with the light guide connection 36 with sleeve 10, which can also be called a "slide". Bayonet ring 35 is constantly positioned on sleeve 10. By rotating the latter, eyepiece 37 and periscope 5 can be detached and moved out to the right.

The details of the invention will be described relative to the components, as obtained on disassembly. Initally, endoscope shaft 6 is released by rotating bayonet lock ring 26 and is drawn away to the left, leaving behind the rest of the instrument partly shown in FIG. 2. To the left, it is once again possible to see gripping arms 1, 2, 3 in a somewhat greater length, whose lowermost part is enveloped by a sleeve 19, which is fixed to shaft closure 13 by two wires 21, 22, whereof only wire 21 can be seen. To the left on sleeve 19, it is possible to see the distal end with the objective of periscope 5, which has a much smaller diameter.

Sleeve 19 merely serves to operate arms 1, 2 and 3 when, as here, endoscope shaft 6 is missing. The possibility also now exists of retracting the arms to the right into sleeve 19. However, they need not be completely inserted as is the case with respect to shaft 6 and need only in fact be inserted to such an extent that the doctor can effortlessly insert the instrument according to FIG. 2 into shaft 6, whilst operating lever 7.

The operating wires 12, which can be seen further to the right, together with an underlying wire 11, belongs to a not visible operating sleeve 4, which is enveloped by sleeve 19. If the locking device 28 is detached in FIG. 2, the wires 11 and 12 can be removed to the left through shaft closure 13, together with gripping arms 1, 2 and 3 and the aforementioned operating sleeve 4.

FIG. 3 shows operating sleeve 4, to which the two operating wires 11, 12 are soldered to the left. They are initially closely juxtaposed in the vicinity of sleeve 4 and are also soldered together. It is only further to the right that they are separated in fork-like manner and have at their ends notches 17, 18 for insertion into the locking device 28. Thus, it is a detachable plug closure. The separation of the two wires 11, 12 is necessary, in order to be able to form two different sliding bearings in shaft closure 13 and these can e.g. be plastic bearings.

FIG. 4 shows another embodiment of the operating sleeve 4, which is formed from two sleeves 4a, 4b, which are interconnected. This is necessary because sleeve 4a must be made from spring steel, if the arms 1, 2, 3 are to be constructed in one piece with sleeve 4a. However, sleeve 4b is made from a harder steel, because it merely serves to operate sleeve 4a. The right-hand part of sleeve 4b is machined in such a way on either side that in this view, only extension 16 is left and behind it is located extension 15.

FIG. 5 shows the right-hand end of sleeve 4b rotated by 90°. It is possible to see here that the machining has left two parts 15, 16, which are spaced from one another. It is also possible according to a third embodiment to remove one of the two parts 15 or 16, so that only one of them is left and is sufficient for operating sleeve 4b. As in FIG. 3, the notches 17, 18 for closure 28 are once again provided at the right-hand end.

Machining of sleeve 4b can take place e.g. by grinding or milling the complete sleeve, so that parts 15, 16 remain.

FIG. 6 shows what is left after the operating sleeve 4 has been dismantled in the aforementioned manner, so that it is the representation of FIG. 2 without sleeve 4.

To the left, it is once again possible to see periscope 5 projecting slightly over sleeve 19. In this case, the two wires 21, 22 are soldered within sleeve 19 and between these wires is located the aforementioned fixed sleeve for periscope 20. The interrupted lines indicate that this sleeve 20 ends at a distance b in front of the left-hand end of sleeve 19, so that there is more space for receiving gripping arms 1, 2, 3. As indicated hereinbefore, there is no need to retract this completely into sleeve 19.

In the shaft closure 13, the interrupted lines indicate the two rivets 38, 39, whereof one is shown by the continuous lines in FIG. 2. This makes it apparent that the arrangement according to FIG. 3 has been rotated by 90° compared with that of FIG. 2. Thus, sleeve 19 is non-detachably connected with the shaft closure 13 by wires 21, 22.

To the extent that it has not already taken place, the operation will be briefly described hereinafter. If handle 40 of lever 7 is moved to the left under the tension of a spring, gripping arms 1, 2, 3 are extended further to the left, so that the periscope objective is also moved to the left, because it follows the movement of slide 14 to the left in a modified scale through sleeve 10.

If handle 40 is now moved to the right, slide 14 moves to the right and through wires 12 moves operating sleeve 4 with gripping arms 1, 2, 3 to the right and draws the latter into endoscope shaft 6. Thus, the gripping arms are operated by the end of the shaft. Periscope 5 is also moved further to the right, not only in order to provide the space with spacing a for the gripping arms, but also for stones or other objects, previously detected under visual observation. During the further movement to the right, periscope 5 is drawn into sleeve 20 behind the end of sleeve 19, so that there is now no possibility of the lens 5 being damaged by a kidney stone or the like.

The invention is not limited to the represented embodiments. For example, it is possible without difficulty to operate completely without sleeve 19 with wires 21, 22, which merely serve to facilitate manipulation on insertion into the shaft. It is also not completely necessary for sleeve 20 to be extended into the endoscope shaft.

However, the main advantage is that the gripping arms can always be easily observed visually through the periscope. Due to the fact that the latter follows, there is an optimum observation in any position of the gripping arms. In addition, there is a further advantage compared with the prior art that it is possible to very easily dismantle the periscope, be detaching bayonet ring 35. In addition, the complete apparatus can be easily drawn out of the conventionally designed endoscope shaft.

What is claimed is:

1. A medical gripping instrument for gripping objects at the distal end of an endoscopy shaft, said shaft having an axis and also having a fixed outer sleeve with a passage opening at said distal end, said instrument comprising:

a periscope disposed on said axis, and axially movable in said shaft;

at least three springy gripping arms axially movable in said shaft and having distal ends thereby coaxially arranged around said axis, and adapted to extend beyond the distal end of the shaft and extend laterally beyond it, whereby to open to receive an object, and to be closed on the object and when drawn into the shaft by contact with the distal end thereby to hold and draw the object toward said shaft, said gripping arms being arranged concentrically around said axis, and leaving a clear path between them along which the periscope can see, said periscope and arms being interlinked so that both move in the same axial direction simultaneously, whereby the region within the arms is in the view of the periscope, and an object brought into the shaft by the arms will not harmfully contact the periscope.

2. An instrument according to claim 1 in which said interlinking of the periscope and gripping arms is attained by a lever system wherein the axial movements of the periscope and of the gripping arms are unequal.

* * * * *